United States Patent
Munn

(10) Patent No.: US 9,724,442 B1
(45) Date of Patent: Aug. 8, 2017

(54) DISINFECTING VANITY MIRROR

(71) Applicant: Max Munn, Tarrytown, NY (US)

(72) Inventor: Max Munn, Tarrytown, NY (US)

( * ) Notice: Subject to any disclaimer, the term of this patent is extended or adjusted under 35 U.S.C. 154(b) by 0 days.

(21) Appl. No.: 15/418,231

(22) Filed: Jan. 27, 2017

(51) Int. Cl.
  *A61L 2/10* (2006.01)
  *A45D 42/00* (2006.01)

(52) U.S. Cl.
  CPC ............... *A61L 2/10* (2013.01); *A45D 42/00* (2013.01)

(58) Field of Classification Search
  CPC .................................. A61L 2/10; A45D 42/00
  USPC ....................... 250/432 R, 435, 504 R, 492.1
  See application file for complete search history.

(56) References Cited

U.S. PATENT DOCUMENTS

| | | | |
|---|---|---|---|
| 6,773,682 B1 | 8/2004 | Benda | |
| 8,662,705 B2 | 3/2014 | Roberts | |
| 8,900,518 B2 | 12/2014 | Seck | |
| 9,308,289 B2* | 4/2016 | Graff | A61L 9/20 |
| 9,480,768 B2 | 11/2016 | Krosney et al. | |
| 2002/0098127 A1* | 7/2002 | Bollini | A61L 9/20 422/121 |
| 2007/0053188 A1 | 3/2007 | New et al. | |
| 2009/0291029 A1 | 11/2009 | Ogasawara et al. | |
| 2012/0199005 A1 | 8/2012 | Koji et al. | |
| 2015/0360606 A1 | 12/2015 | Thompson et al. | |
| 2017/0007736 A1 | 1/2017 | Engelhard | |

FOREIGN PATENT DOCUMENTS

| | | |
|---|---|---|
| CN | 202526007 | 11/2012 |
| CN | 202629828 | 12/2012 |
| CN | 203633880 | 6/2014 |
| CN | 205561091 | 9/2016 |
| KR | 20120133286 | 12/2012 |

OTHER PUBLICATIONS

Official Publication of the International Ultra Violet Association, IUV ANews http://www.iuva.org/Publications.

* cited by examiner

*Primary Examiner* — Michael Maskell
(74) *Attorney, Agent, or Firm* — Myron Greenspan Lackenbach Siegel LLP

(57) ABSTRACT

A disinfecting vanity mirror includes a mirror panel having a top end and a bottom end when mounted on a wall. A mirror hanger mounts the mirror panel in spaced relation to the wall to create a plenum space behind the mirror panel that is open at the top and bottom ends to provide a vertical air passageway through the plenum space for air entering through the bottom end to rise and exit through the top end. A source of UV-C light is provided along the bottom end to promote convection by locally heating air to sanitize the air moving upwardly through said plenum space where it is exposed to the UV light. A heating element is provided near the bottom end to more quickly heat the air to accelerate movement of the air to be recycled and increased numbers of pathogens to be exposed to the UV-C light source.

20 Claims, 4 Drawing Sheets

US 9,724,442 B1

DISINFECTING VANITY MIRROR

BACKGROUND OF THE INVENTION

1. Field of the Invention

This invention generally relates to vanity mirrors and, more specifically, to vanity mirrors that disinfect and purify air by exposing pathogens to a source of ultraviolet (UV) light within the range of 200-280 nm for use in medical and other facilities.

2. Description of the Background Art

Health care-associated infections (HAIs) in hospitals, assisted living facilities, etc., are serious and mostly preventable health problems. It has been estimated that HAIs cause or contribute in excess of 99,000 deaths annually in the United States. Various bacteria become immune or resistant to disinfectants applied to surfaces in hospitals and other medical facilities, these bacterias commonly cause what are being referred to as "staph" infections because they are resistant to many chemical disinfectants used to clean counter tops and other surfaces in hospital rooms and the like. The general problem is discussed, for example, in the Official Publication of the International Ultra Violet Association, IUVANews. http://www.iuva.org/Publications Various UV devices have been proposed to reduce infectious pathogens. For example, bathrooms in airplanes have started to use UV LED strips to reduce pathogens while in flight. Other facilities are being outfitted with various devices to expose pathogens to UV light sources. However, UV light sources have generally been independent or stand alone devices that are specifically designed for intermittent applications.

SUMMARY OF THE INVENTION

In order to address the above and other problems associated with sanitizing or sterilizing airborne pathogens it is an object of the invention to provide a disinfecting vanity mirror that serves the additional function of exposing airborne pathogens and those on countertops to ultraviolet light to neutralize such pathogens and makes them ineffective or less effective.

It is another object of the invention to provide a disinfecting vanity mirror as in the previous object that is simple in construction and economical to manufacture.

It is still another object of the invention to provide a disinfecting vanity mirror as in the previous objects that is simple and convenient to install above a countertop in medical and other facilities that require surface and air purification.

It is yet another object of the invention to provide disinfecting vanity mirror of the type under discussion that promotes and accelerates the flow of air to be sanitized or sterilized by heating the air and causing it to rise by convention past a UV-C source of light.

It is an additional object to the invention to provide a disinfecting, vanity mirror that incorporates a UV-C source of light that is safe to occupants, effective, non-obtrusive and aesthetically pleasing and provides continuous and reliable anti-bacterial sanitizing action both by being in proximity to a countertop and by re-cycling air to insure enhanced exposure of the bacteria to UV radiation.

It is still an additional object of the invention to provide a method of sanitizing or sterilizing airborne bacteria by incorporating a UV-C source of light along a bottom edge of a vanity mirror above a countertop (e.g. 10" above the surface) and heating the air as it rises through a plenum space behind the mirror to the UV-C light source.

To achieve the above objects and others that will become evident hereinafter, a disinfecting vanity mirror in accordance with the invention comprises a mirror panel having a top end and a bottom end when mounted on a wall. Mounting means is provided for mounting the mirror panel on a vertical surface above a countertop in spaced relation from the vertical surface to create a plenum space between said mirror panel and the vertical surface that is open at the top and bottom ends to provide a "chimney-like" substantially vertical air passageway or column through said plenum space for rising air entering through the bottom end and existing through top end. A source of UV light is provided substantially along at least a portion of the bottom end to promote convection by locally heating air at the proximate said bottom end, whereby the UV light sanitizes air moving upwardly through the plenum space where it is exposed to the UV light.

A method in accordance with the invention comprises the steps of disinfecting or sterilizing countertop surfaces and air of medical and assisted living facilities, workspaces and other enclosures having vanity mirrors with a predetermined spacing from a wall to create a plenum space behind the mirror; providing UV light at a lower end of the mirror to heat the air and cause it to rise through said plenum space to expose pathogens in the air to the UV-C light in the range of 100-280 nm. The air at the lower end of the plenum space is advantageously heated to promote and accelerate movement of air through the plenum space to recycle the air and enhance air purification and elimination of pathogens.

BRIEF DESCRIPTION OF THE DRAWINGS

Those skilled in the art will appreciate the improvements and advantages that derive from the present invention upon reading the following detailed description, claims, and drawings, in which:

DESCRIPTION OF PREFERRED EMBODIMENTS

Figure 2:
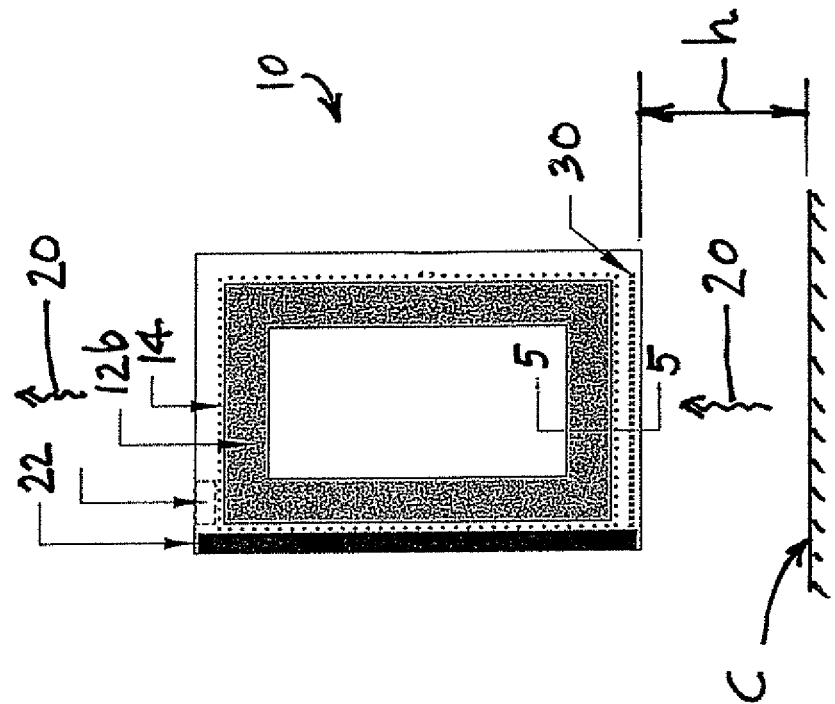
FIG. 2 is a rear elevational view of the mirror shown in FIG. 1.
Figure 1:
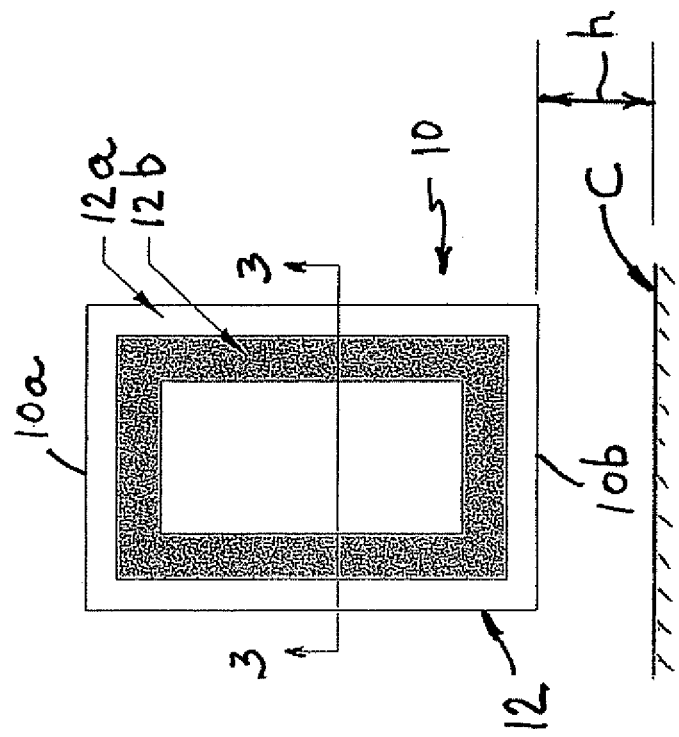
FIG. 1 is a front elevational view of a disinfecting vanity mirror in accordance with the present invention.
Figure 3:
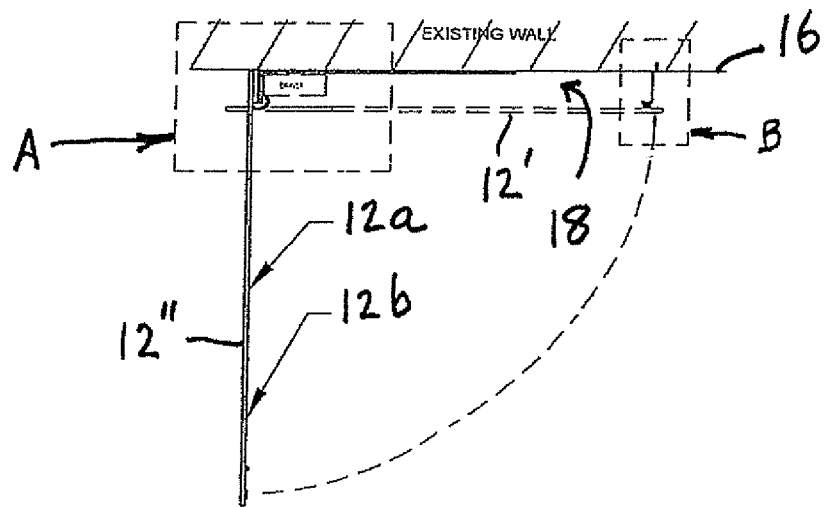
FIG. 3 is a top plan view of the mirror as shown in FIGS. 1 and 2, with the mirror panel in an open position.

Referring now specifically to the figures, in which the identical or similar parts are designated by the same reference numerals throughout, and first referring to FIG. 1, a disinfecting vanity mirror in accordance with the invention is generally designated by the reference numeral 10.

In the preferred embodiment, the mirror 10 is generally rectangular in shape as shown and includes a top end 10a and a bottom end 10b. The mirror 10 includes a mirror panel 12 having a central reflective surface 12a and a frosted peripheral strip 12b. The mirror panel 12 may be 3/16" clear hospitality grade mirror. The mirror 10 may be similar in appearance to back-lit mirrors of the type manufactured by MunnWorks LLC in Mount Vernon, N.Y. LED Strip 14 emitting visible light, for example, at 2700k provides lighting through the frosted peripheral strip 12b in a conventional manner.

Referring to FIGS. 2-5, the mirror 10 is typically mounted on a wall or vertical surface 16 above a countertop C to create a plenum space 18 between the mirror panel 12 and the mounting surface. The plenum space 18 has openings at the top and bottom ends, 10a, 10b to provide a substantially vertical air shaft, passageway or column for air to rise by entering through the bottom end 10b and exiting through the top end 10a as suggested by the arrows 20 in FIG. 2. While the height of the mirror 10 above the countertop C is not critical a typical height of 10" is typical and will provide beneficial germicidal results in the application of the invention.

Referring specifically to FIGS. 3-6, a method of mounting the mirror 10 is illustrated. A mirror hanger 22 is provided that includes a major mounting portion 22a and a minor mounting portion 22b. As indicated, the major mounting portion 22a is generally coextensive with the wall 16 while the minor mounting portion 22b is provided at one lateral side of the major mounting portion and projects in an outward direction generally normal to the major mounting portion away from the wall 16 when mounted on the wall. Provided along the vertical free edge of the minor mounting portion 22b is a hinge 24 to movably mount the mirror panel 12 between a normally closed position 12', shown in dash outline, substantially parallel to the wall to create the plenum space 18 and an open position 12", shown in solid line in FIGS. 3 and 4, to provide access to the plenum space 18. In the embodiment shown, the mirror panel 12 is spaced a distance d approximately 2" from the wall 18 to provide the plenum space 18 with a depth somewhat less than the dimension d.

Figure 4:
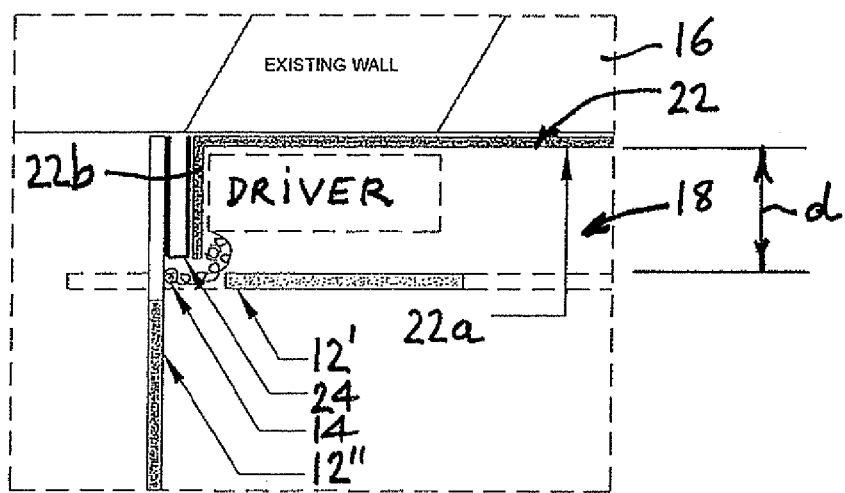
FIG. 4 is an enlarged view of detail A shown in FIG. 3.
Figure 5:
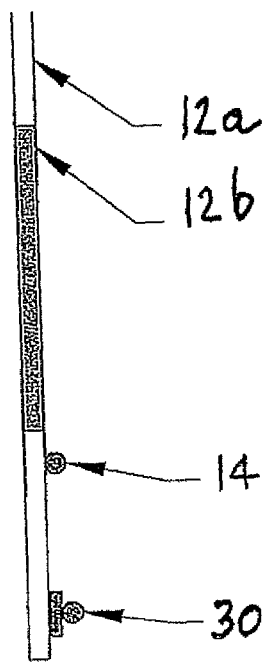
FIG. 5 is an enlarged fragmented cross-sectional view of the lower region of the mirror shown in FIG. 2, taken along line 5-5.
Figure 6:
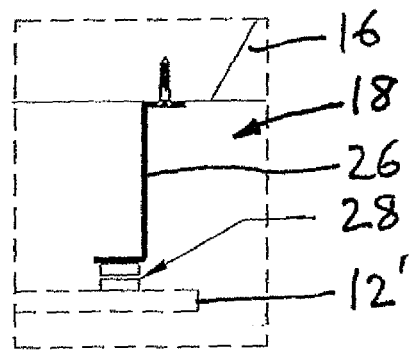
FIG. 6 is an enlarged view of detail B shown in FIG. 3.

Any suitable or conventional hinge can be used to mount the mirror panel 12. However, as shown in FIG. 4, a U-shaped plastic hinge 24 is preferred for this application to eliminate or minimize the number of interstices or crevasses in which pathogens can become lodged and multiply. In order to maintain the mirror panel 12 in its normally closed position parallel to the wall 18 a suitable stopper or spacer 26 is provided that maintains the position of the mirror panel in its closed position at spacing d from the wall 18 to keep the mirror panel in a desired position and to ensure the integrity of the plenum space 18. The spacer or stopper 26 is shown to include a magnet 28 on the mirror panel 12 to prevent inadvertent movement of the mirror panel from its closed position.

An important feature of the present invention is the integration of a source of UV light 30 that extends along at least a portion but preferably along the entire width of the bottom end 10b to promote convection of air by locally heating air proximate to the bottom end 10b to generate airflow 20. The UV light sanitizes air moving upwardly through the plenum space 18, created to simulate a chimney effect, and promote movement of air past the UV light source 30. Also, by providing the UV light source 30 in proximity to the lower end or edge of the mirror 10 the UV light will be efficient in sanitizing or neutralizing pathogens on the countertop C.

In accordance with a presently preferred embodiment the UV light source 30 is in the form of a strip of LEDs that emit UV light within the range of 200-280 nm and, preferably within the range of 240-280 nm. As indicated in the IUVANews publication ultraviolet radiation is defined most broadly as consisting of radiation within the range of 10-400 nm. However, most effective for germicidal applications is the short wave ultraviolet light normally designated as UV-C. UV-C includes wavelengths of 100-280 nm, although 240-280 nm are most effective for sanitizing or sterilizing airborne pathogens. UV light in that range is most efficiently absorbed by DNA, with maximum absorption being at approximately 260 nm. UV-C has been used for air purification, sterilization and disinfection. High intensity UV at 240-280 nm radiation can destroy DNA in living micro organisms. The effectiveness of the UV radiation is directly related to intensity and exposure time. The present disinfecting vanity mirror 10 is convenient, inexpensive and an effective way to neutralize micro-organisms and pathogens by constantly circulating and recycling the air that passes through the plenum space 18, forcing the air to be continuously exposed to the UV LED-strip 30.

Figure 8:
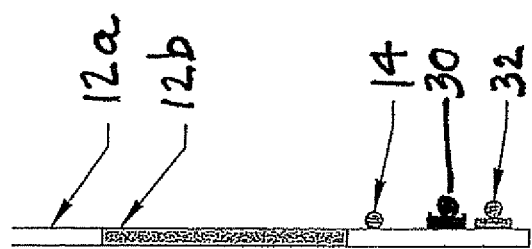
FIG. 8 is similar to FIG. 5 but of the mirror shown in FIG. 7, taken along line 8-8.
Figure 7:
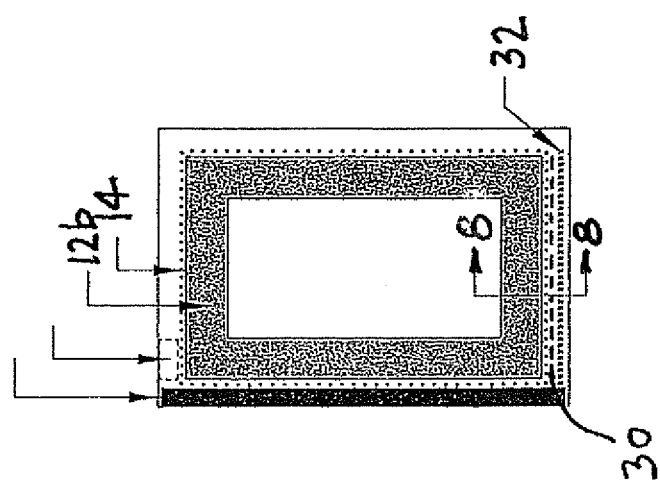
FIG. 7 is a rear elevational view of an alternate embodiment of a disinfecting vanity mirror in accordance with the present invention.

To enhance the quantity of air moved through the plenum space 18 the present invention advantageously utilizes a thermal strip 32, shown in FIGS. 7 and 8, for providing additional heating of the air in proximity to the UV LED strip 30 at the bottom end 10b of the mirror. Between the heating of the air by the UV LED strip 30 and the thermal strip 32 the air below the vanity mirror 10 is heated more quickly and more vigorously and to a higher temperature. This causes higher quantities of air to move up through the plenum space 18 thereby exposing increased numbers of pathogens to the UV light source 30.

By using a mirror 10, for example, that is 24-30" wide and 34-40" tall at a height of approximately 10" above a sink or countertop C most harmful pathogens can be neutralized if power is applied for only approximately 30 minutes per day. The LED strips are conventionally powered when a wall switch is turned on (e.g. in a bathroom where a sink, countertop and vanity mirror are typically situated). Normally the vanity is used at least 30 minutes per day.

The disinfecting vanity mirror 10 is, therefore, an inexpensive and reliable way of exposing air contaminated with pathogens to UV-C light on an ongoing or continuing basis when energized to increase the effectiveness of the sanitization and decontamination of airborne and surface of microorganisms found on countertops.

By locating the UV light source 30 along the bottom edge of the mirror, behind the mirror panel 12, a number of advantages are achieved. The user is protected from UV radiation that can be harmful to the user's eyes and skin. Also, the light does not reflect onto the mirror to avoid undesirable shades or tones or lighting distortions. Using LED light strips considerably increases the life of the sources over conventional UV sources, such as mercury lamps or bulbs. By integrating the UV light source into the vanity mirror there is no need to have an operator use specialized UV equipment to periodically sanitize a facility.

The method of the present invention is, therefore, to position a mirror panel 12 of a vanity mirror 10 a predetermined space from a wall of a medical facility, work space or other chamber where vanity mirrors are utilized to create a plenum space 18 behind the mirror. UV light is then provided at the lower end of the mirror to heat the air and cause it to rise through the plenum space and expose pathogens in the air to the UVC light in the range of 10-400 nm and preferably 240-280 nm. An optimum wavelength is approximately 260 nm.

The method advantageously includes the additional step of providing enhanced heating of the air to promote movement of the air through the plenum space. This accelerates exposure of the air to be disinfected or sterilized to the UV light. This can be achieved by placing a thermal strip at the lower end of the mirror.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. Disinfecting vanity mirror comprising a mirror panel having a top end, a bottom end and lateral edges when mounted on a wall; mounting means for mounting said mirror panel on a vertical surface in spaced relation to the vertical surface to create a plenum space between said mirror panel and the vertical surface that is open at said top and bottom ends to provide a substantially vertical air passageway through said plenum space for rising air entering through said bottom end and exiting through said top end; and a source of UV light within or in proximity to the plenum space to expose air and surfaces in proximity to the plenum space to UV light, whereby the UV light sanitizes air moving upwardly through the plenum space and proximate surfaces exposed to the UV light.

2. A vanity mirror as defined in claim 1, wherein said mirror panel is rectangular and said top end is coextensive with one side of said rectangular panel and said bottom end is coextensive with and opposing side of said rectangular panel.

3. A vanity mirror as defined in claim 1, wherein said mounting means includes a wall bracket attachable to a blocking in a wall.

4. A vanity mirror as defined in claim 3, wherein said mounting means includes a mirror hanger attachable to said wall bracket.

5. A vanity mirror as defined in claim 4, wherein said mirror hanger includes a major mounting portion attachable to said wall bracket and a minor mounting portion at one lateral side of said major mounting portion and projecting in a direction substantially normal to said major mounting portion away from said bracket when mounted on a wall.

6. A vanity mirror as defined in claim 5, wherein said mirror mounting portion forms a substantially vertical free edge when the mirror is mounted on a wall, and said mounting means includes a hinge at said vertical free edge to movably mount said mirror panel between a normally closed position substantially parallel to the mounting wall to create said plenum space and an open position to provide access to said plenum space.

7. A vanity mirror as defined in claim 6, wherein said hinge is a plastic hinge.

8. A vanity mirror as defined in claim 1, wherein said source of UV light comprises a strip of LEDs emitting UV light within the range of 200-280 nm.

9. A vanity mirror as defined in claim 1, further comprising means for heating air proximate to said bottom end to promote movement of air by convection through said plenum space part said source of UV light.

10. A vanity mirror as defined in claim 9, wherein said means for heating comprises a thermal strip.

11. A vanity mirror as defined in claim 1, wherein said source of UV light generate ultraviolet C radiation within the range of 100-280 nm.

12. A vanity mirror as defined in claim 11, wherein the UVC radiation is in the range of 240-280 nm.

13. A method of disinfecting or sterilizing air of medical facilities, workspaces and other chambers having vanity mirrors comprising the steps of positioning a vanity mirror a predetermined spacing from a wall to create a plenum space behind the mirror; and providing UV light within or in proximity to the plenum space to expose pathogens in the air within the plenum space or surfaces proximate to the plenum space to the UVC light in the range of 100-280 nm.

14. A method as defined in claim 13, further providing heating means for heating of air to promote movement of air through said plenum space and accelerate exposure of air to be disinfected or sterilized by said UV light.

15. A method as defined in claim 14, wherein said heating means is provided by a thermal strip at the lower end of the mirror.

16. A method as defined in claim 13, wherein UVC light is selected to be within the range of 240-280 nm.

17. A method as defined in claim 13, wherein the UVC light is provided by a strip of LEDs in proximity to a lower end of said mirror.

18. Disinfecting vanity mirror comprising a mirror panel having a top end, a bottom end and lateral edges when mounted on a wall; mounting means for mounting said mirror panel on a vertical surface in spaced relation to the vertical surface to create a plenum space between said mirror panel and the vertical surface that is open at said top and bottom ends to provide a substantially vertical air passageway through said plenum space for rising air entering through said bottom end and exiting through said top end; and a source of UV light within or in proximity to the plenum space to expose air and surfaces in proximity to the plenum space to UV light, whereby the UV light sanitizes air moving upwardly through the plenum space and proximate surfaces exposed to the UV light, said mounting means including a hinge at one of said lateral edges to movably mount said mirror panel between a normally closed position substantially parallel to the mounting wall to create said plenum space and an open position to provide access to said plenum space.

19. Disinfecting vanity mirror comprising a mirror panel having a top end, a bottom end and lateral edges when mounted on a wall; mounting means for mounting said mirror panel on a vertical surface in spaced relation to the vertical surface to create a plenum space between said mirror panel and the vertical surface that is open at said top and bottom ends to provide a substantially vertical air passageway through said plenum space for rising air entering through said bottom end and exiting through said top end, wherein said mounting means includes a hinge at one of said vertical edge to movably mount said mirror panel between a normally closed position substantially parallel to the mounting wall to create said plenum space and an open position to provide access to said plenum space; wherein a source of UV light is provided within or in proximity to the plenum space to expose air and surfaces in proximity to the plenum space to UV light.

20. A vanity mirror as defined in claim 19, wherein said mounting means includes a wall bracket attachable to a wall and a mirror hanger attachable to said wall bracket and a major mounting portion attachable to said wall bracket and a minor mounting portion at one lateral side of said major mounting portion and projecting in a direction substantially normal to said major mounting portion away from said bracket when mounted on a wall.

* * * * *